US012725250B2

(12) United States Patent
Kim et al.

(10) Patent No.: US 12,725,250 B2
(45) Date of Patent: Sep. 1, 2026

(54) METHOD FOR EXECUTING APPLICATION HAVING IMPROVED SELF-DIAGNOSIS ACCURACY FOR HAIR, AND SELF-DIAGNOSIS SERVICE DEVICE FOR HAIR BY USING SAME

(71) Applicant: AFS INC., Seoul (KR)

(72) Inventors: Taehee Kim, Seoul (KR); Hojong Lee, Seoul (KR); Hojeong Cha, Seoul (KR); Chan-il Jeong, Seoul (KR); Donghyeon Lee, Goyang-si (KR)

(73) Assignee: AFS INC., Seoul (KR)

( * ) Notice: Subject to any disclaimer, the term of this patent is extended or adjusted under 35 U.S.C. 154(b) by 469 days.

(21) Appl. No.: 18/038,983

(22) PCT Filed: Oct. 8, 2021

(86) PCT No.: PCT/KR2021/013878
§ 371 (c)(1),
(2) Date: May 25, 2023

(87) PCT Pub. No.: WO2022/114508
PCT Pub. Date: Jun. 2, 2022

(65) Prior Publication Data

US 2024/0005486 A1 Jan. 4, 2024

(30) Foreign Application Priority Data

Nov. 26, 2020 (KR) ........................ 10-2020-0161134
Nov. 26, 2020 (KR) ........................ 10-2020-0161212

(51) Int. Cl.
*G06K 9/00* (2022.01)
*A61B 5/00* (2006.01)
(Continued)

(52) U.S. Cl.
CPC .......... *G06T 7/0012* (2013.01); *A61B 5/0077* (2013.01); *A61B 5/448* (2013.01);
(Continued)

(58) Field of Classification Search
CPC .............................. G06T 7/0012; A61B 5/448
See application file for complete search history.

(56) References Cited

U.S. PATENT DOCUMENTS

2017/0354466 A1* 12/2017 Zhang .................... A61B 5/448
2018/0214072 A1* 8/2018 Zingaretti .............. A61B 5/448
2019/0340671 A1* 11/2019 Tran .................. G06Q 30/0643

FOREIGN PATENT DOCUMENTS

JP 06-090932 A 4/1994
KR 10-2013-0029482 A 3/2013
(Continued)

OTHER PUBLICATIONS

Kim, T., et al., PCT/KR2021/013878, International Search Report, Jan. 14, 2022, 5 pages.
(Continued)

*Primary Examiner* — Molly Wilburn
*Assistant Examiner* — Aidan Keup
(74) *Attorney, Agent, or Firm* — Rahman LLC

(57) ABSTRACT

In the present invention, virtual stereoscopic information is extracted from two-dimensional images of a user's hairline to identify the depth of the head and hairline information; it recommends a hairline that harmonizes with the user's hairline shape and/or overall facial shape, measures the approximate hair density at the forehead line, and determines the required number of hairs depending on the chosen hairline shape; the invention automatically diagnoses the required hair count, promotes the necessity of hair transplantation, and enhances the accuracy of hair self-diagnosis; this is achieved through an application execution method
(Continued)

and a hair self-diagnosis service device that utilizes the same.

12 Claims, 14 Drawing Sheets

(51) Int. Cl.

| | |
|---|---|
| ***G06T 7/00*** | (2017.01) |
| ***G06T 7/13*** | (2017.01) |
| ***G06T 7/593*** | (2017.01) |
| ***G06T 7/60*** | (2017.01) |
| ***G06T 19/00*** | (2011.01) |
| ***G06V 40/16*** | (2022.01) |
| ***G16H 20/40*** | (2018.01) |

(52) U.S. Cl.

CPC ................ *G06T 7/13* (2017.01); *G06T 7/593* (2017.01); *G06T 7/60* (2013.01); *G06T 19/00* (2013.01); *G06V 40/165* (2022.01); *G06V 40/171* (2022.01); *G16H 20/40* (2018.01); *G06T 2200/04* (2013.01); *G06T 2200/24* (2013.01); *G06T 2207/10012* (2013.01); *G06T 2207/10028* (2013.01); *G06T 2207/30088* (2013.01); *G06T 2207/30201* (2013.01); *G06T 2207/30242* (2013.01)

(56) References Cited

FOREIGN PATENT DOCUMENTS

| | | | |
|---|---|---|---|
| KR | 10-2017-0086829 | A | 7/2017 |
| KR | 10-1870689 | B1 | 8/2017 |
| KR | 10-2018-0106752 | A | 10/2018 |
| KR | 10-2019-0123067 | A | 10/2019 |
| KR | 10-1946466 | B1 | 10/2019 |

OTHER PUBLICATIONS

Kim, T., et al., PCT/KR2021/013878, Written Opinion, Jan. 14, 2022, 8 pages.

* cited by examiner

METHOD FOR EXECUTING APPLICATION HAVING IMPROVED SELF-DIAGNOSIS ACCURACY FOR HAIR, AND SELF-DIAGNOSIS SERVICE DEVICE FOR HAIR BY USING SAME

TECHNICAL FIELD

The present invention aims to provide a method for executing an application that enhances hair self-diagnosis accuracy and a hair self-diagnosis service device using the same by extracting virtual stereoscopic information from user hairline photos captured in a two-dimensional form, identifying head depth information and hairline information, proposing a hairline that harmonizes with the user's hairline shape and/or overall facial shape, measuring the approximate hair density of the forehead hairline, and automatically diagnosing the necessary number of hairs depending on whether the hairline shape is selected, thereby heightening the need for hair transplantation.

DESCRIPTION OF RELATED ART

In modern society, the number of people suffering from hair loss has been steadily increasing due to stress, poor eating habits, and genetic factors, leading to an increase in concerns related to hair loss; in addition to hair loss, there is a growing trend of people wanting to adjust their hairlines for cosmetic purposes, such as making their faces appear smaller or achieving a natural-looking hairline.

In the past, there were two methods for self-diagnosing hair loss: individuals personally filling out a checklist, and using a hair loss self-diagnosis application.

In the case of filling out a checklist for hair loss self-diagnosis, the user would directly check off items based on their own judgement rather than comparing it with precise comparison data, and this led to a problem where an objective assessment of the progression stage of hair loss was difficult because the checklist was filled out based on the user's judgement.

On the other hand, the method of diagnosing hair loss through an application, which involved taking images with a standard camera during user photo capture, led to inconsistencies in aspects of the head part, such as the slope and depth information of the forehead, making it impossible to accurately identify the shape and size of the head and, consequently, using only 2D images without depth information to determine the shape of the head resulted in a large margin of error, diminishing the practicality of self-diagnosis.

Therefore, even when conducting self-diagnosis, there was a problem where the practicality of self-diagnosis decreased as it either recommended a suitable hairline for the user, or provided a uniform number of necessary hair follicles without allowing the user to select the desired hairline.

[Patent Document 1] Korean Issued Patent Gazette No. 10-1870689 (Issued on Jun. 19, 2018)

To address the aforementioned issues, the present invention aims to provide a hair self-diagnosis service device and an application that extracts virtual stereoscopic information from user hairline photos captured in a two-dimensional form to identify head depth information and hairline information or measures the head of a person with hair loss in three dimensions using a depth camera, minimizes errors in the number of required hair follicles, proposes a hairline that suits the overall shape of the user's head, and the position and proportion of the eyes, nose, and mouth, measures the approximate density of the hair that forms the end of the user's bangs, determines the number of necessary hair follicles depending on whether the hairline shape is chosen to diagnose the required number of hairs to enhance the need for hair transplantation, provides hair care solutions, generates revenue through advertising marketing that links with hair transplant surgery hospitals of related hospitals, sets alarms at regular intervals to capture and compare changing hairlines, and allows users to self-monitor their progress after hair transplant surgery.

BRIEF SUMMARY

In order to achieve the above purpose, the method for executing the application that improves the accuracy of hair self-diagnosis according to the present invention initially generates and stores 3D (three-dimensional) user head image information based on image data obtained by photographing at least one direction from the front, left side, right side, or top of the user's head; the user head image captured in a two-dimensional is mapped to the 3D user head image information, and the density of the reference hair, for example, the hair density located at the boundary of the hairline, is automatically analyzed; the application includes allowing the user to (i) select a recommended hairline suitable for the user's face shape or (ii) set the hairline directly, then visualizing it, for example, displaying it, and providing the calculated number of required hairs based on the selected or set hairline.

Additionally, the hair self-diagnosis service device according to the present invention includes a hair self-diagnosis body, for example, that has a quadrangular frame structure, which the user holds with both hands and positions in front of their face while facing forward, to measure the depth of the head and photograph the user's hairline; the application also identifies the depth information and hairline information of the head photographed by the hair self-diagnosis body, automatically analyzes the density of the reference hair, for example, the hair density located at the boundary of the hairline, and allows the user to (i) select a recommended hairline suitable for the user's face shape or (ii) set the hairline directly; the application visualizes the selection or setting, provides the calculated number of required hairs based on the visualized image, and includes a hair self-diagnosis application.

As described above, in the present invention, by extracting virtual stereoscopic information from user hairline photos captured in a two-dimensional form or measuring the head of a person with hair loss in 3D through a depth camera, the error in the required number of hairs is minimized; a suitable hairline is proposed to harmonize with the user's overall head shape, the position and proportion of the eyes, nose, and mouth, and the approximate density of the hair at the end of the user's forehead is measured; depending on the selection of the hairline shape, the number of required follicles is determined, automatically diagnosing the required number of hairs, promoting the need for hair transplantation, providing hair care solutions, generating revenue through advertising marketing linked to affiliated hair transplant surgery hospitals, setting alarms at regular intervals to take pictures, and having the beneficial effect of being able to self-diagnose the progress after hair transplant surgery by identifying comparison photos of changing hairlines.

DETAILED DESCRIPTION OF EXAMPLE EMBODIMENTS

Hereinafter, a preferred embodiment according to the present invention will be described with reference to the accompanying drawings.

Figure 1:
FIG. 1 is a block diagram showing the overall components of the hair self-diagnosis service device according to the present invention.
Figure 2:
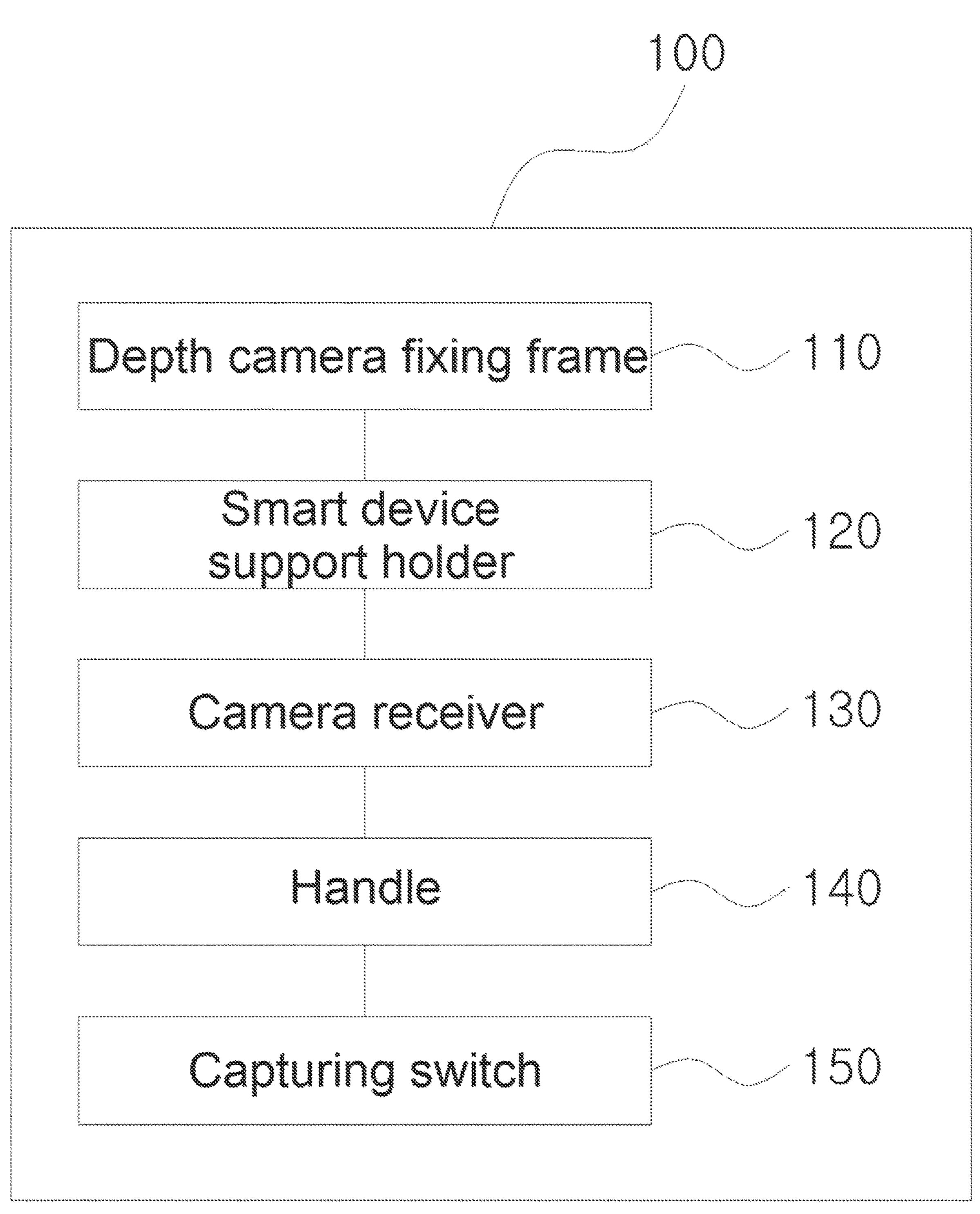
FIG. 2 is a block diagram showing the components of the hair self-diagnosis body according to the present invention.
Figure 3:
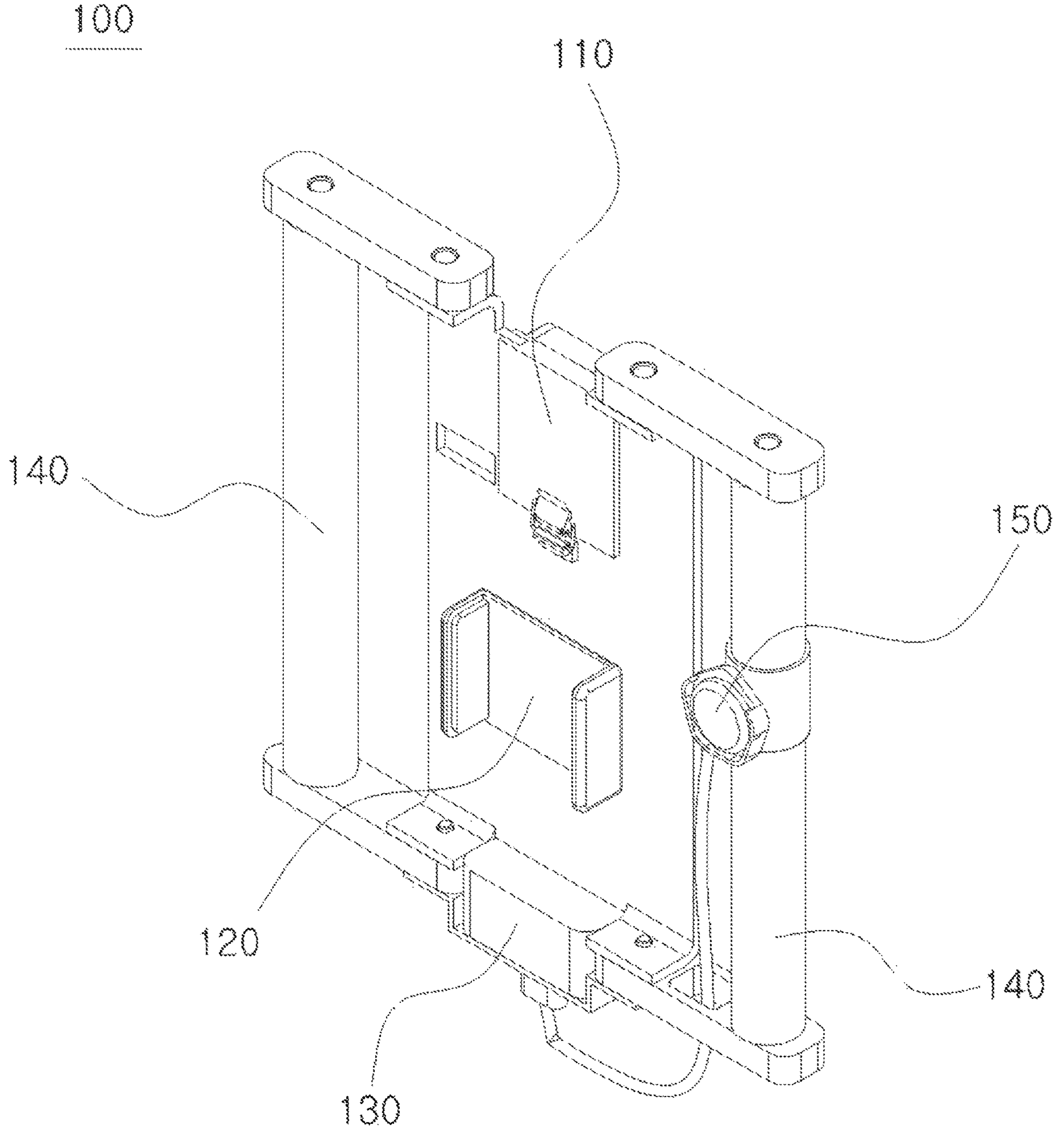
FIG. 3 is a perspective view showing the overall shape of the hair self-diagnosis body according to the present invention.
Figure 4:
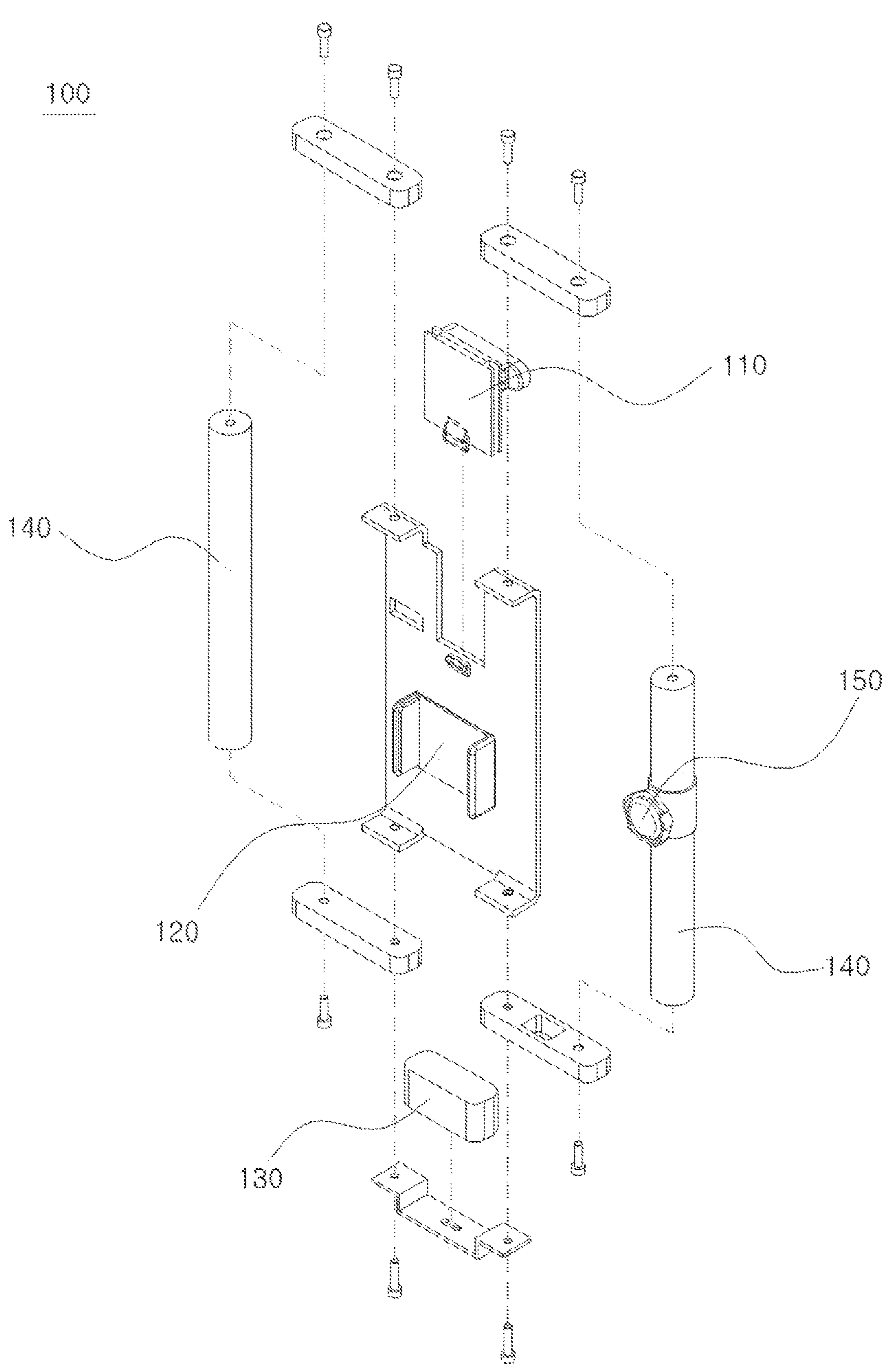
FIG. 4 is an exploded perspective view showing the components of the hair self-diagnosis body according to the present invention.
Figure 5:
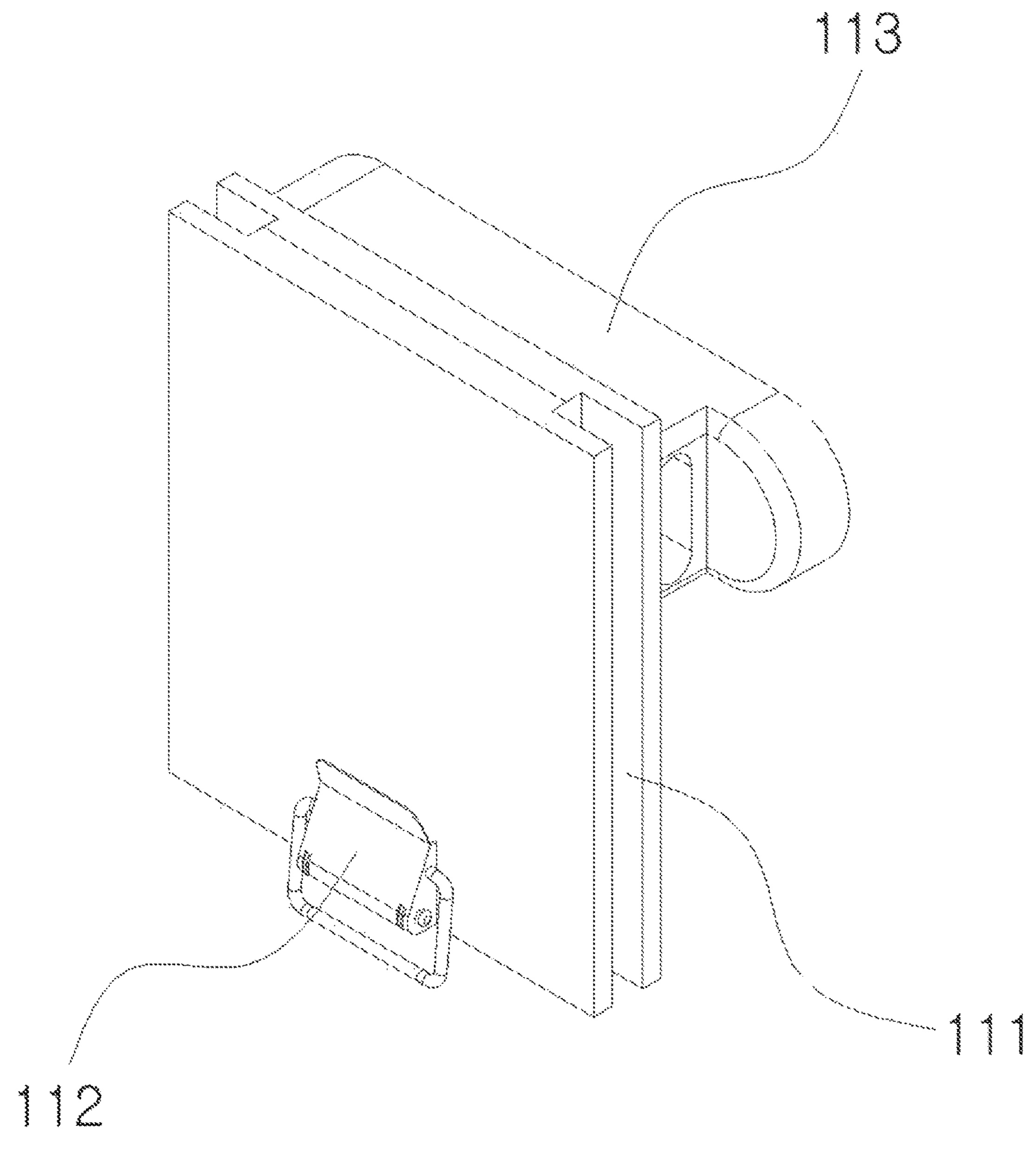
FIG. 5 is a perspective view showing the components of the depth camera fixing frame according to the present invention.
Figure 6:
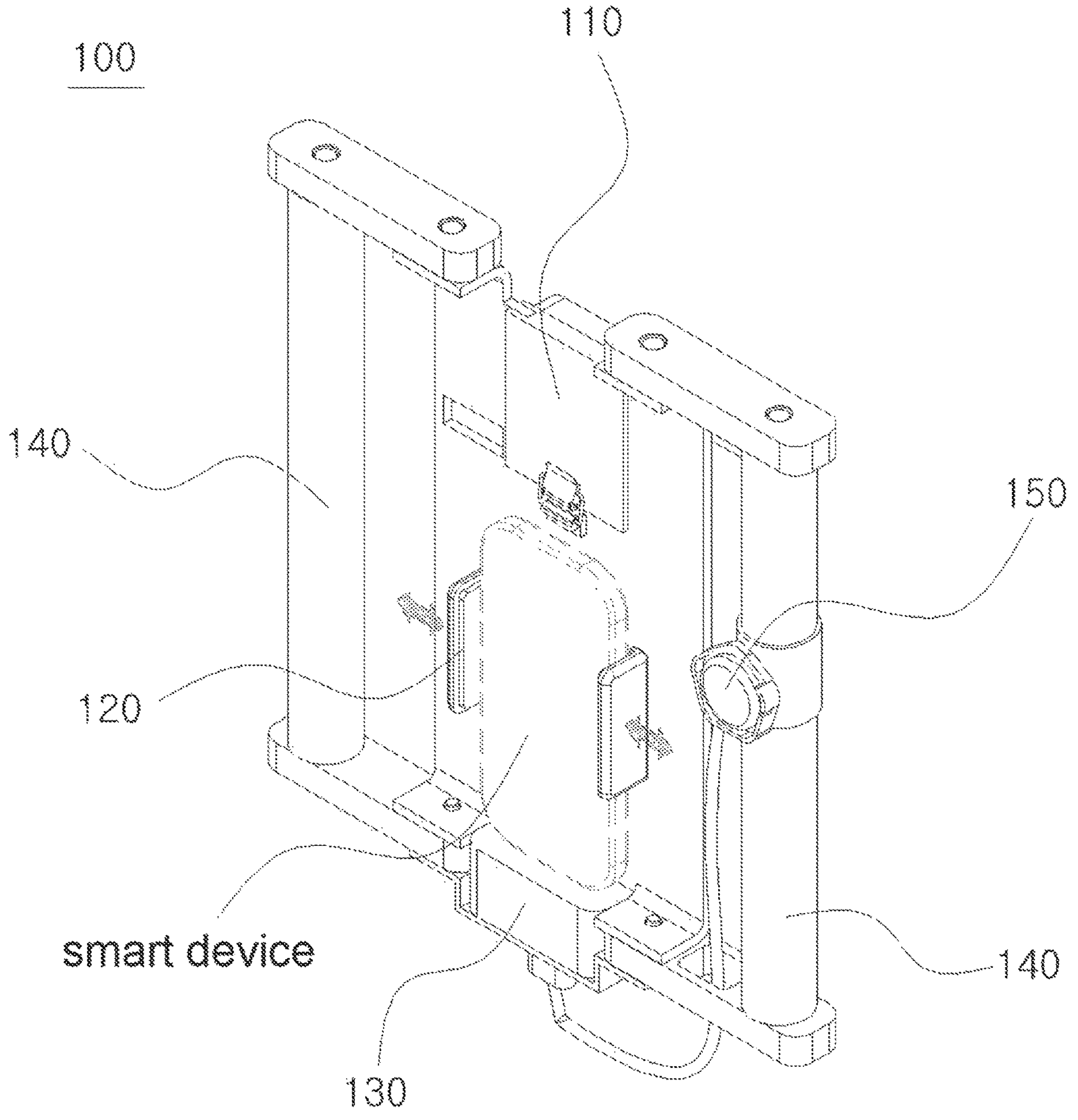
FIG. 6 is an exemplary view showing a state in which a smart device is combined with the smart device support holder of the hair self-diagnosis body according to the present invention.
Figure 7:
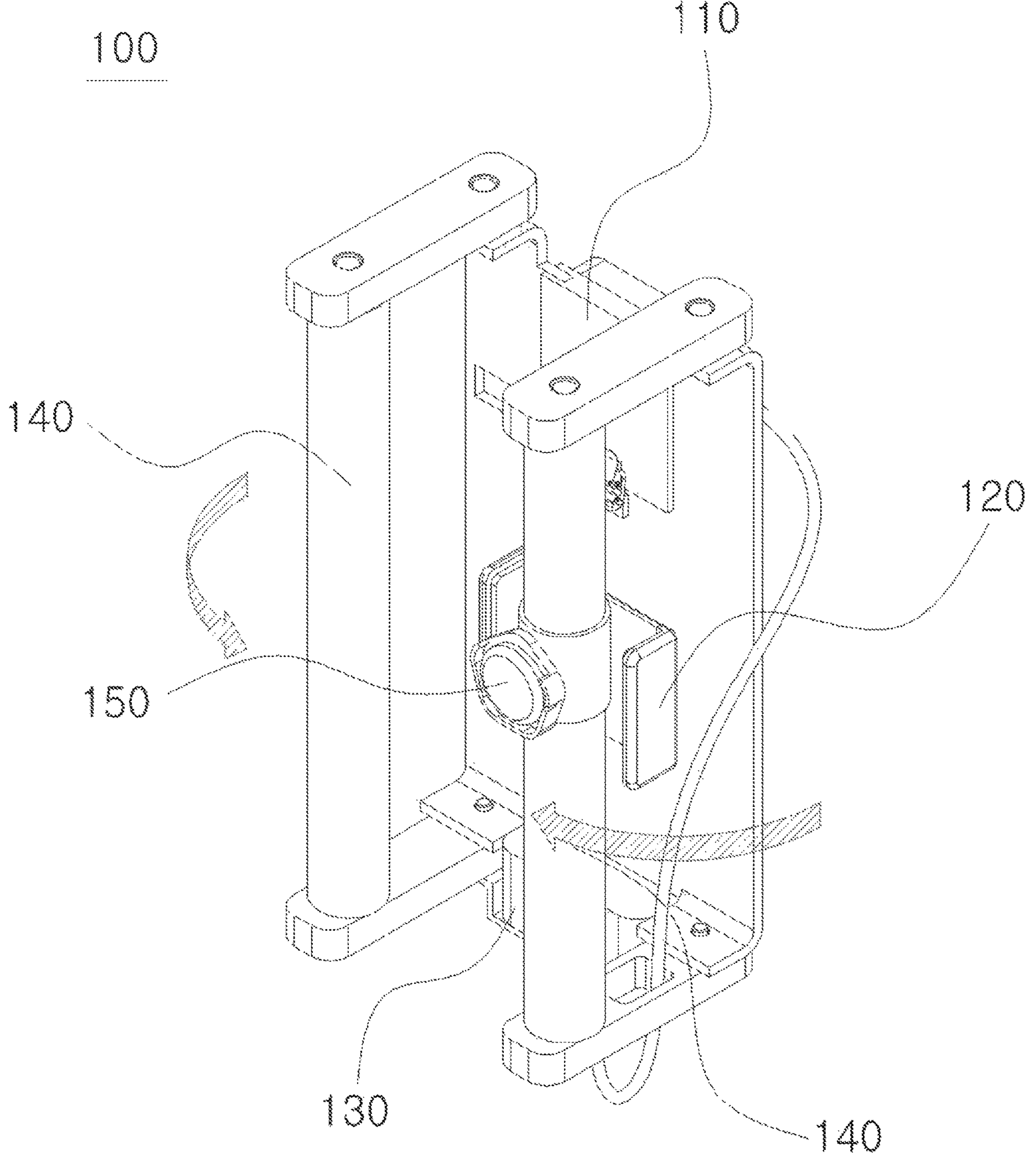
FIG. 7 is an exemplary view showing a state in which the left and right handles of the hair self-diagnosis body according to the present invention are rotated and folded to reduce the volume.

FIG. 1 is a block diagram showing the overall components of a hair self-diagnosis service device according to the present invention, which includes a hair self-diagnosis body (100) and a hair self-diagnosis application (200).

First, the hair self-diagnosis body (100) according to the present invention will be described.

In one embodiment, the hair self-diagnosis body (100) is a quadrangular frame structure which the user holds with both hands while facing forward, places in front of their face, measures the depth of the head, and photographs the user's forehead hairline. The description of the hairline in this specification is not limited to the forehead hairline and can be easily applied to other hairlines, which a person with ordinary skill in the art (hereinafter referred to as "those ordinarily skilled in the art") can understand.

This can include a depth camera fixing frame (110), a smart device support holder (120), a camera receiving device (130), a handle (140), and a capturing switch (150).

The depth camera fixing frame (110) is a quadrangular frame structure that can be attached/detached by a sliding structure at the top center of the hair self-diagnosis body, and it supports the depth camera that is attached to the central front.

The depth camera fixing frame (110) according to the present invention is formed with rail grooves (111) on the left and right sides of the quadrangular frame structure in the vertical length direction, inserted into the top center of the hair self-diagnosis body by sliding, and a fastening element (112) is formed at the bottom center of the quadrangular frame to prevent the depth camera fixing frame from moving or shaking, and a depth camera (113) connected to the camera receiving device wirelessly or wired is formed at the upper center of the rear of the quadrangular frame.

The smart device support holder (120) serves to stably support the user's smart device, which is attached to the holder, by adjusting based on the shape and size of the smart device the spacing of the clips supporting the left and right sides of the smart device.

The smart device support holder (120) according to the present invention is configured so that the smart device clip supporting the smart device on the left and right sides is moved in the left and right directions and restored to its original position by an internal spring so that it can be mounted in various smart device sizes.

The camera receiving device (130) receives depth capture data captured by the depth camera via wired, Bluetooth, and Wi-Fi network transmission and sends it to the smart device.

The camera receiving device (130) according to the present invention is connected to the depth camera attached to the depth camera fixing frame (110), the smart device attached to the smart device support holder (120), and the capturing switch (150) wirelessly or wired, and when the capturing switch is pushed, the 3D captured image data from the depth camera is stored in the smart device.

The handle (140) is formed as a cylindrical bar shape in the vertical length direction, symmetrically on the left and right sides of the Hair self-diagnosis body, allowing the user to grip the hair self-diagnosis body stably with both hands.

The capturing switch (150) is formed as a button structure or touch structure shape on one side of the top of the handle, and performs the shooting function through Bluetooth transmission with the depth camera and smart device.

The hair self-diagnosis body (100) shown in FIG. 1 is merely an example, and it would be understood by those ordinarily skilled in the art that the structure of the hair self-diagnosis body (100) is not limited to this.

Figure 8:
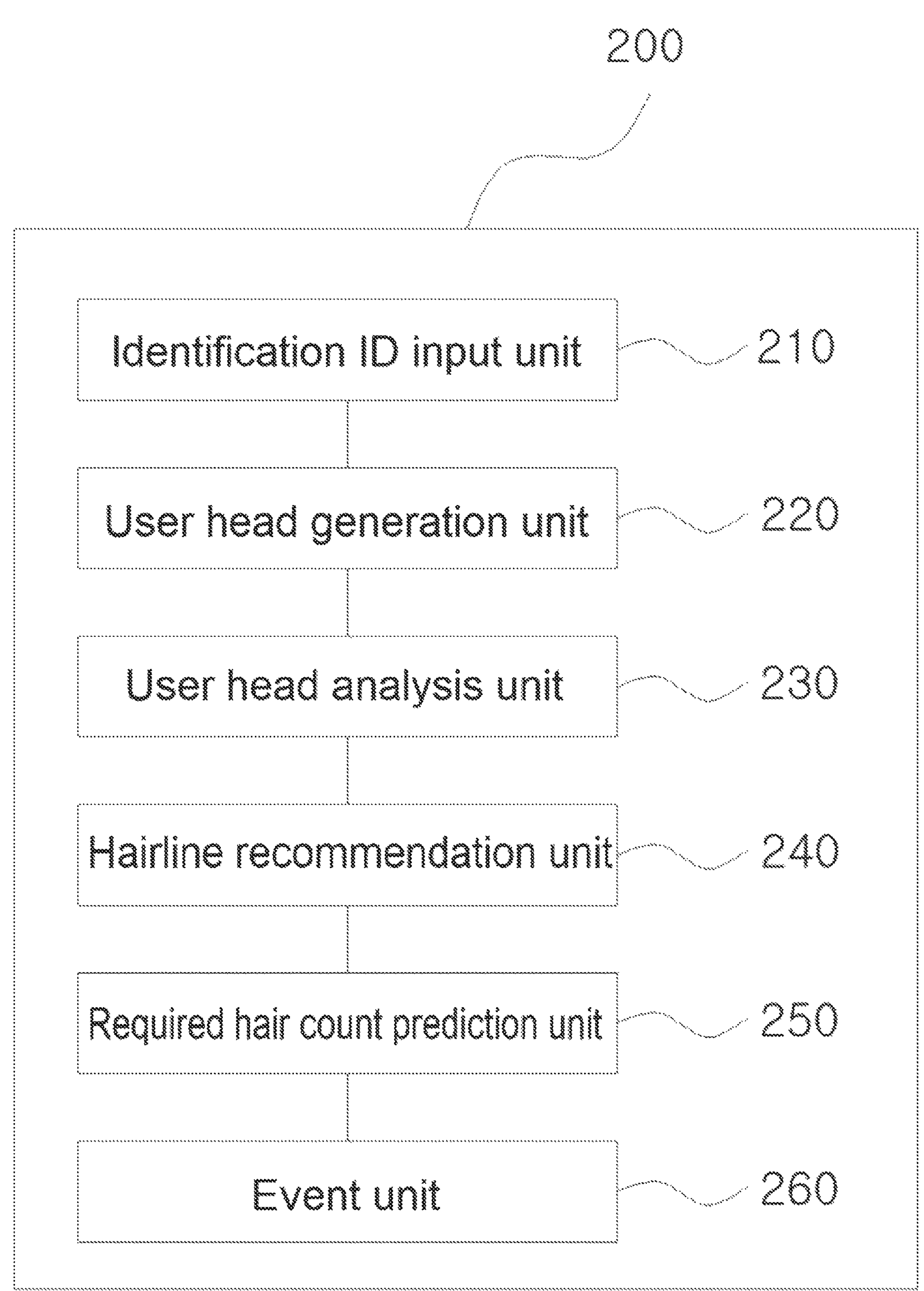
FIG. 8 is a block diagram showing the overall components of the method for executing the application that improves the accuracy of hair self-diagnosis according to the present invention.
Figure 9A:
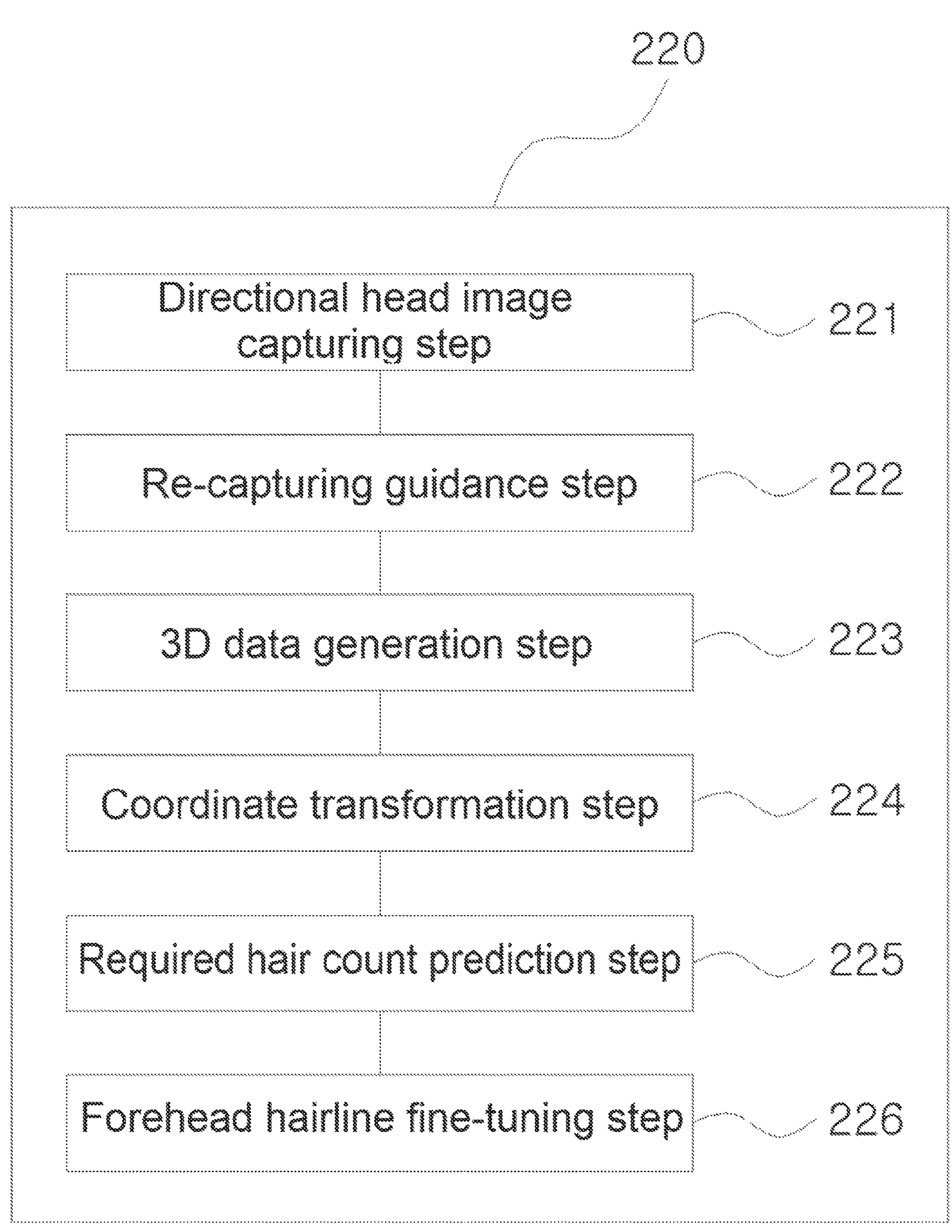
FIG. 9*a* is a block diagram showing the components of the user head generation unit according to the first embodiment of the present invention.
Figure 9B:
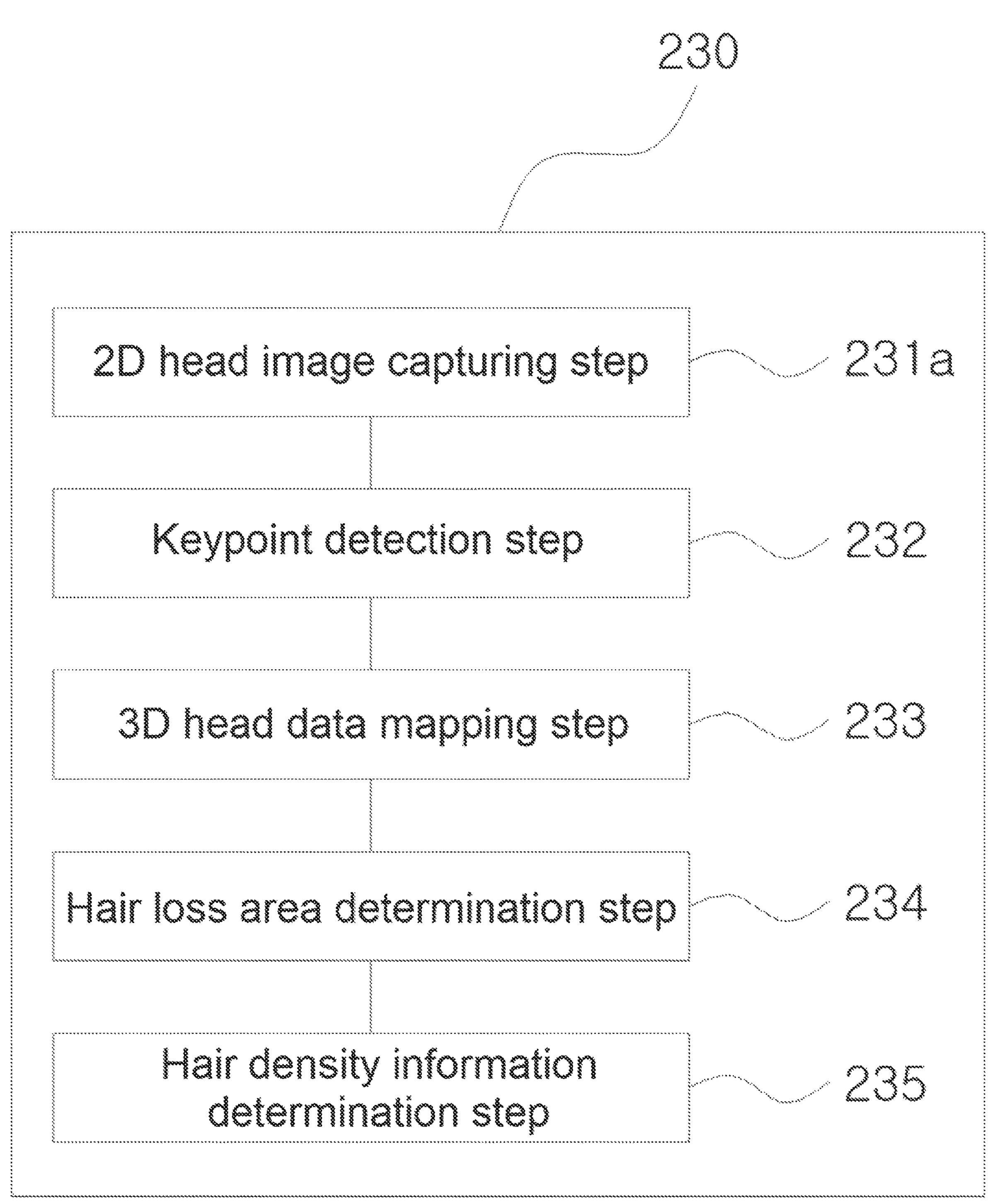
FIG. 9*b* is a block diagram showing the components of the user head analysis unit according to the first embodiment of the present invention.
Figure 9C:
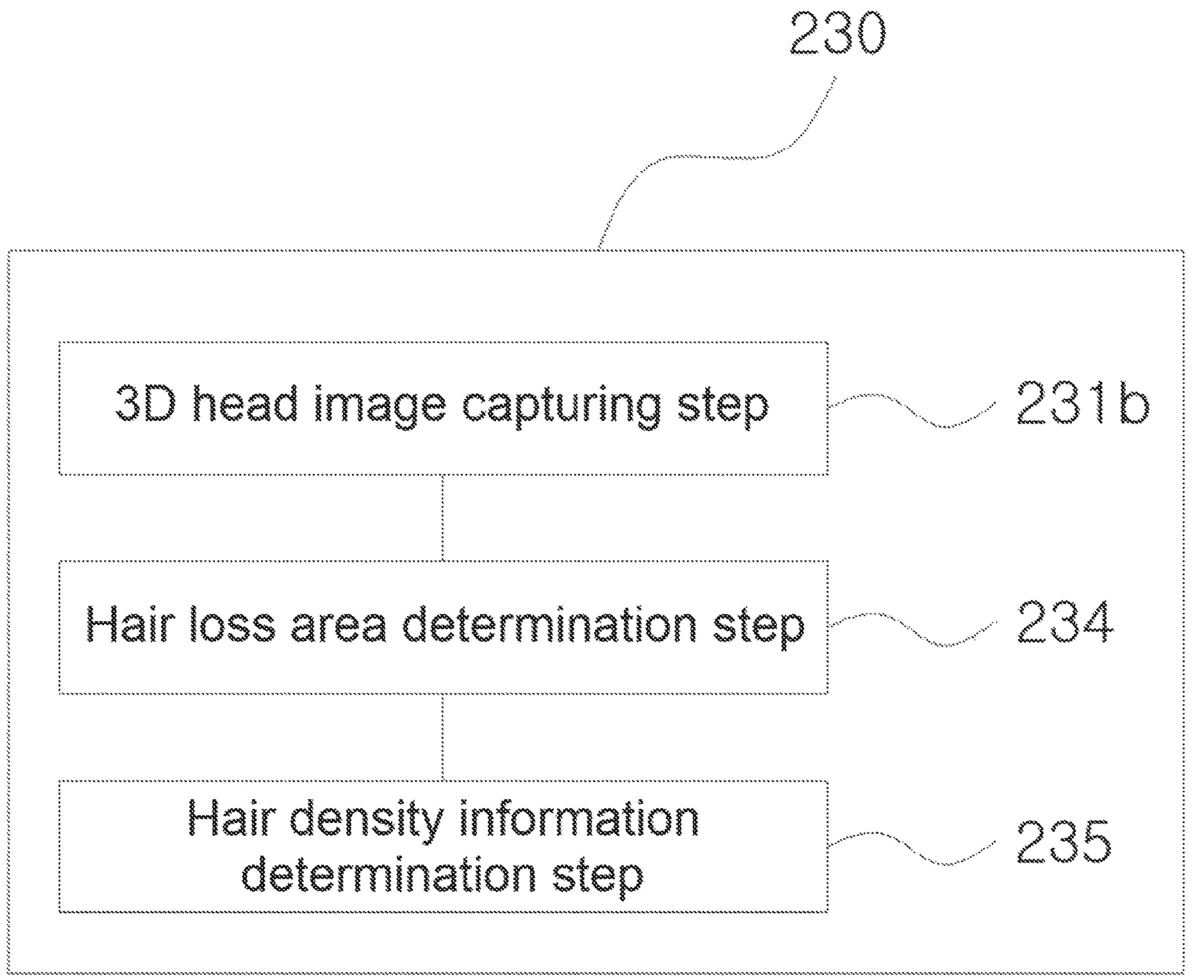
FIG. 9*c* is a block diagram showing the components of the user head analysis unit according to the second embodiment of the present invention.
Figure 10:
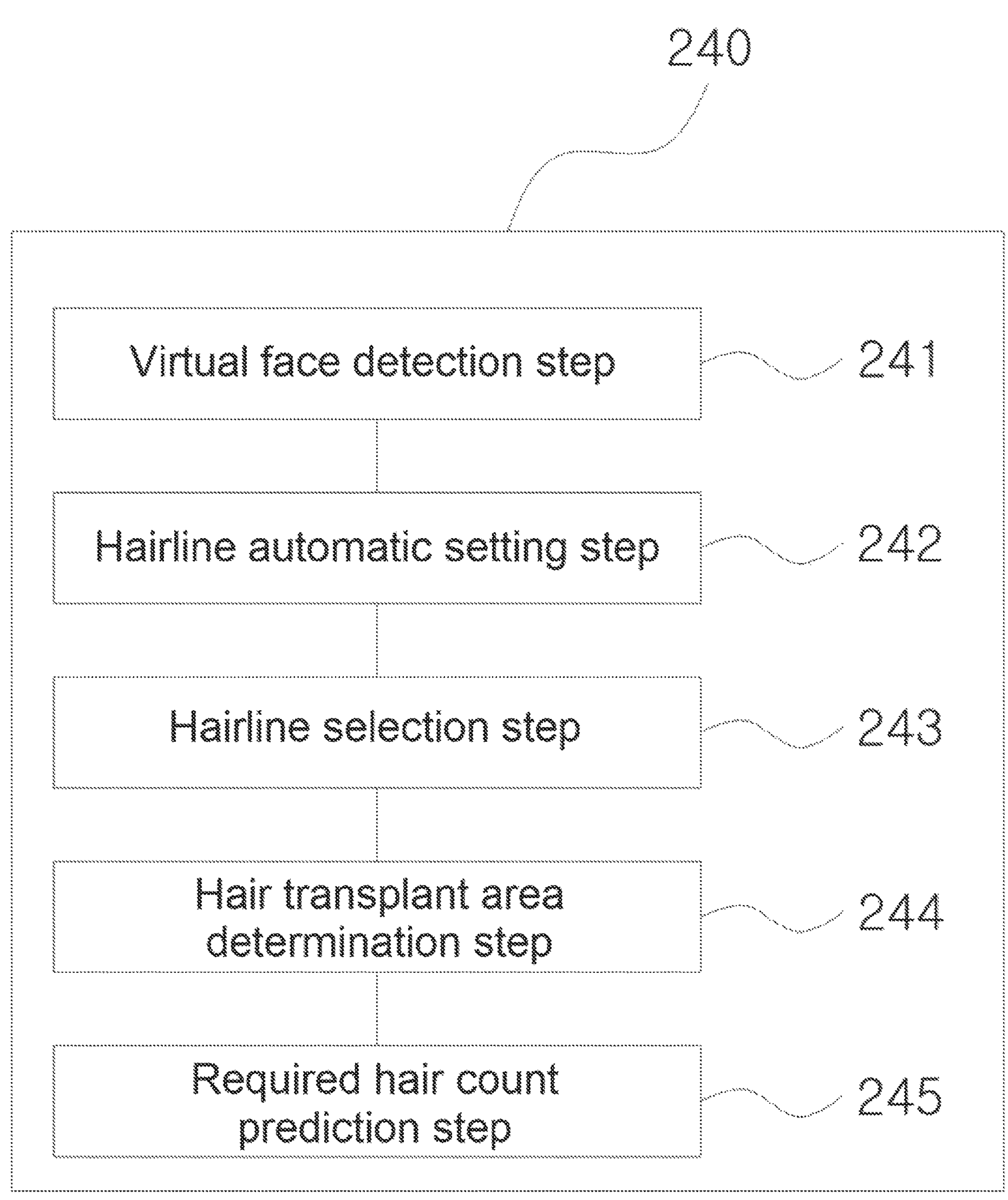
FIG. 10 is a block diagram showing the components of the hairline recommendation unit according to the present invention.
Figure 11:
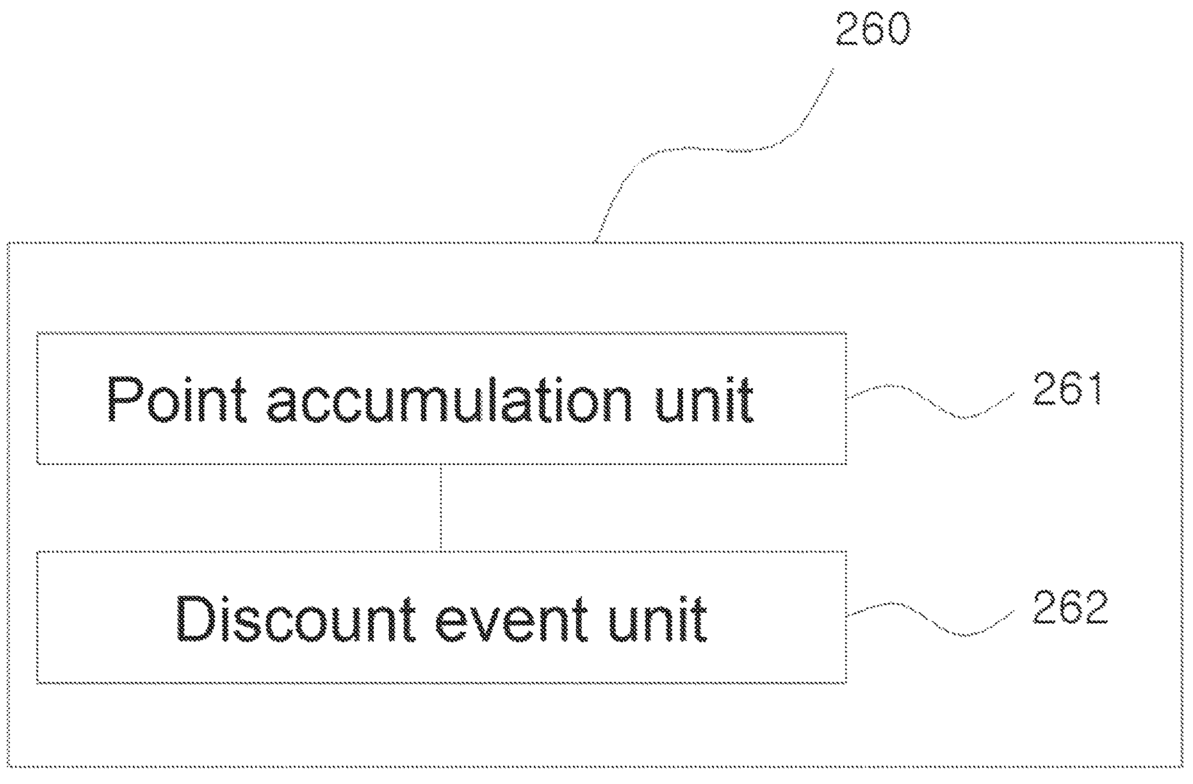
FIG. 11 is a block diagram showing the components of the event unit according to the present invention.
Figure 12:
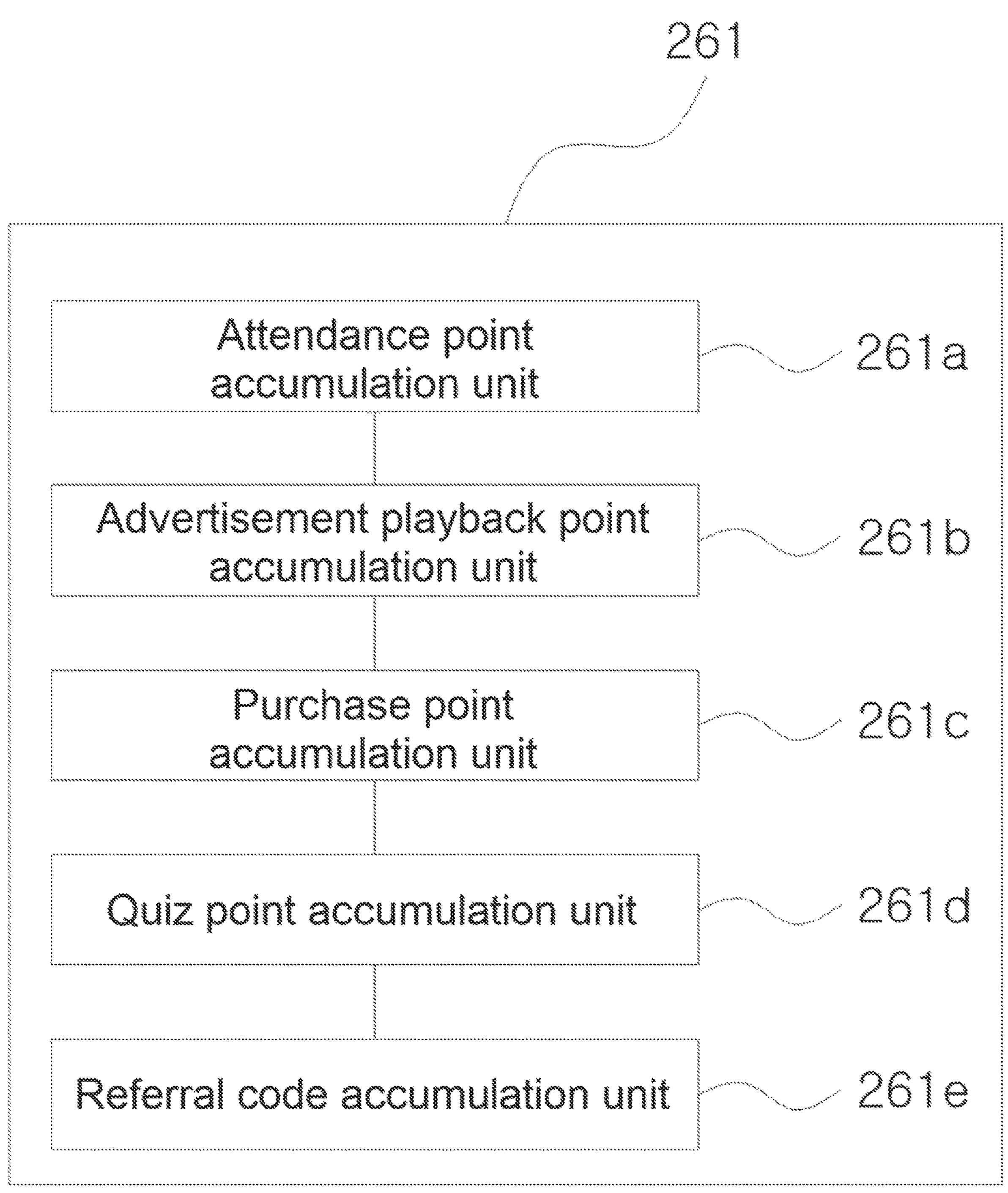
FIG. 12 is a block diagram showing the components of the point accumulation unit according to the present invention.

FIG. 8 is a block diagram illustrating the overall components of an application execution method for improving the accuracy of hair self-diagnosis according to the present invention.

Referring to FIG. 8, the hair self-diagnosis application (200) according to the application execution method initially generates and stores a 3D user head image information based on 2D image data obtained by photographing at least one direction of the user's head front, left, right, and top without using a depth camera in the first embodiment; the user head photos captured in a two-dimensional form can be mapped to the 3D user head image information.

As an alternative, in the second embodiment using a depth camera, the hair self-diagnosis application (200) identifies the user's head depth information and forehead hairline information captured by the depth camera in the hair self-diagnosis body.

Subsequently, the hair self-diagnosis application (200) according to the first and second embodiments automatically analyzes the density of the reference hair, for example, the hair density located at the boundary of the forehead hairline, (i) recommends a hairline suitable for the user's face shape, for example, based on big data analysis, which the user can select, or (ii) if the user directly sets the forehead hairline, the application visualizes and displays it, and calculates and provides the required hair count according to the selected or set forehead hairline.

For this purpose, the hair self-diagnosis application (200) according to the present invention may include a user head analysis unit (230), a hairline recommendation unit (240), and a required hair count prediction unit (250). Additionally, the hair self-diagnosis application (200) may further include an identification ID input unit (210).

In the first embodiment, the hair self-diagnosis application (200) further includes a user head generation unit (220).

First, the identification ID input unit (210) according to the present invention is described. The identification ID input unit (210) assigns an identification ID to identify the individual information to be self-diagnosed, and stores the user's personal information data such as race, gender, age, etc., according to the identification ID setting. Additionally, the identification ID input unit (210) can further store the user's name and the user's 3D facial image data captured through the hair self-diagnosis body. Of course, the identification ID input unit (210) is not an essential component of the hair self-diagnosis application (200).

This is because the hair self-diagnosis application can assign an identification ID to each user and classify personal information by the assigned identification ID, and store not only the user's name, gender, age, etc., but also the user's head capture information, access date information, hairline change information over time, and other personal information data through the user's login; it is understood by those skilled in the art that an identification ID does not necessarily need to be assigned.

Moreover, the identification ID input unit (210) can set an alarm for head image shooting at regular intervals, allowing the user to periodically self-diagnose the progress of hair loss, changes due to hair management, and progress after hair transplant surgery by taking comparison photos of the changing hairline at regular intervals.

Next, the user head generation unit (220) according to the first embodiment of the present invention is described.

The user head generation unit (220) captures and stores the user's head in a panorama form, for example, from the left to the right direction or from the front to the top direction, or in the form of directional stepwise 2D multi-angle head data for each identification ID input in the identification ID input unit; it identifies stereoscopic shape of the user's head based on the panorama form or the directional stepwise 2D multi-angle head data and creates a 3D user head image; it detects at least one key point information of the body parts constituting the user's head part, such as eyes, nose, mouth, ears, forehead, and hairline, to create a customized 3D head data for the first time.

The user head generation unit (220) can perform the directional head image capturing step (221), the 3D data generation step (223), for instance, forming a point cloud, the coordinate transformation step (224), the user head stereoscopic information generation step (225), and the forehead hairline fine-tuning step (226) sequentially. In one embodiment, a re-capturing guidance step (222) can be performed between the directional head image capturing step (221) and the 3D data generation step (223).

The directional head image capturing step (221) captures at least one image of the user's head viewed in at least one direction, including a predetermined direction or an arbitrary direction, within the face recognition area of the hair self-diagnosis application. This is to reproduce the user's hair loss area in 3D. Here, the image of the user's head viewed in the predetermined direction can be at least one of the left image, front-left image, front image, front-right image, right image, frontal upper image, and top image of the user's head, but the image of the user's head looking in an arbitrary direction not included therein can also be captured in the directional head image capturing step (221).

When two or more images are captured, they can be captured so that they can be combined with each other. For example, in the directional head image capturing step (221), one of the left image, front-left image, front image, front-right image, right image, frontal upper image, and top image of the user's head and another image looking at the user's head in an arbitrary direction can be captured.

This is carried out in the initial full head capture mode and the initial image interpolation capture mode of the hair self-diagnosis application.

Here, when the initial full head capture mode is set, an oval face recognition area is formed in the center of the smart device screen, and when at least one or any direction image of the left side, front-left, front, front-right, right side, frontal upper, or top images is captured within 80-95% of the size in the face recognition area of the hair self-diagnosis application according to the user's head capture direction, it is automatically scanned and captured.

This allows the user to conveniently capture parts of their head by aligning the smart device screen so that at least one or any direction image of the left side, front-left, front, front-right, right side, frontal upper, or top images is reflected; this automatically captures the image within the face recognition area.

Here, when the initial image interpolation capture mode is set, an oval face recognition area is formed in the center of the smart device screen, and when any one or more of the left image, front-left image, front image, front-right image, right image, frontal upper image, top image, or an arbitrary direction head direction image is caught within 80-95% of the size in the face recognition area of the hair self-diagnosis application according to the user head capture direction, it is automatically scanned and captured.

This is used in situations where the overall capture image of the user's head cannot be secured.

Specifically, when the initial image interpolation capture mode detects at least one user head direction capture information, for example, based on big data stored in the hair self-diagnosis application server or web server, it detects standard head information corresponding to the most similar ethnicity to the user head direction capture information and matches the detected head information with at least one head direction capture information to interpolate the uncaptured part of the user's head.

In this way, the 3D user head information obtained by each individual through the hair self-diagnosis application (200) can be additionally stored in the hair self-diagnosis application server or web server and can be used as big data for later captured user head information.

The re-capturing guidance step (222) detects when the captured angle of at least one or an arbitrary direction image of the left image, front-left image, front image, front-right image, right image, frontal upper image, top image is significantly deviated from the angle set based on at least one body part constituting the user's head part, for example, eyes, nose, mouth, ears, forehead, and hairline, or is not clearly captured, and guides re-capturing.

This identifies at least one of the captured user's body parts, e.g., eyes, nose, mouth, ears, forehead, and hairline, to guide the recapture of the portion of the head that needs to be recaptured if the angle of each part's image of the head within the face recognition area is off, or if each part's image of the head that needs to be recaptured is detected to be out of focus or shaky in each part's image of the head that is automatically scanned and captured in the directional head image capturing step.

This ensures in the position-wise capture that the user's head is captured with a clear image in the face recognition area and that accurate head part capture is carried out within the set angle.

The 3D data generation step (223) involves detecting the x, y, and z-axis positional coordinates position by position in the reference coordinate system for at least one or any direction image of the captured left-side image of the user's head, front-left image of the head, frontal image of the head, front-right image of the head, right-side image of the head, frontal-top image of the head, and top image of the head, forming point clouds or mesh models, among other 3D data formats.

This entails detecting the x, y, and z-axis positional coordinates of each part's image of the head captured in the directional head image capturing step and forming them into a 3D data format.

Meanwhile, it is known that even if only a single 2D image of the user's head is captured, 3D data of the user's head can be inferred using machine learning. For, in this case, it is sufficient if the amount of 3D data necessary for the diagnosis by this invention is formed, not the entire head of the user.

The necessary 3D data for diagnosis, for example, refers to the forehead's 3D data when confirming frontal hair loss and the crown's 3D data when confirming crown hair loss. However, it is common to want to check for hair loss in multiple areas, 3D data that includes the line from the forehead to the crown is generally needed. There may also be cases where 3D data for the occipital area is necessary, but the areas where 3D data can be formed are not limited to the examples mentioned.

The coordinate transformation step (224) serves to transform the x, y, and z-axis positional coordinates of at least one or any direction image of the left-side image, front-left image, frontal image, front-right image, right-side image, frontal-top image, and top image of the user's head, which are formed in 3D data format, into a single coordinate system.

This involves transforming the positional coordinates generated from the part capture images of the head captured in the directional head image capturing step into a single coordinate system.

The user head stereoscopic information generation step (225) infers based on or integrates at least one and/or any direction image of the left-side image, front-left image, frontal image, front-right image, right-side image, frontal-top image, and top image of the user's head, which have been transformed into a single coordinate system, to create 3D user head stereoscopic information.

This represents the user's head images as a single x, y, z positional coordinate through the coordinate transformation step, and generates user-customized 3D stereo data in the same shape as the user's head.

The user head stereoscopic information generation step (225) according to the present invention can create user-customized 3D head data with minimized error range for the overall head through the user's directional head images when the initial whole head capture mode is selected in the directional head image capturing step (221).

According to the present invention, the user head stereoscopic information generation step (225) can, in the case where the initial image interpolation capture mode is selected in the directional head image capturing step (221), match at least one of the user's directional head images with the most similar standard head image, interpolate the uncaptured parts of the user's head, and generate the user's virtual 3D head stereo data, even if the overall capture image of the user's head is not secured. The aforementioned most similar standard head image, for example, can be detected based on big data stored on a hair self-diagnosis application server or web server.

The aforementioned forehead hairline fine-tuning step (226) serves to finely tunes the 3D information of the user's head part, for example, the forehead area and the forehead hairline area, from the 3D user head stereoscopic information. In one embodiment of the forehead hairline fine-tuning step (226), a high-resolution 2D camera can be additionally utilized to finely tunes the aforementioned 3D information obtained from a depth camera.

This allows for a fine-tuning of the head part such as the forehead area and forehead hairline area in the user-customized 3D data created in the user head stereoscopic information generation step to grasp the user's forehead hairline and hair density.

According to the present invention, the user head generation unit (220) can initially create user-customized 3D head data by capturing at least one or any directional image among left, front-left, front, front-right, right, front-top, and top images, depending on the user's smart device model with a built-in depth camera function and the user head capture direction; the more images captured, the more accurate the shape can be created based on depth capture data.

Alternatively, the user head generation unit (220) according to the second embodiment of the present invention can generate the 3D head data by capturing a 3D user head image using a depth camera.

Depth cameras mentioned in this disclosure may include stereo depth cameras, infrared (IR) depth cameras, and ToF cameras, but are not limited thereto.

For reference, 3D data acquired by a depth camera can be managed and stored in various types such as point clouds and RGBD. The 3D data can be simultaneously captured, combined with information captured while the shooting device moves around the subject user's head, or captured at multiple angles while rotating the subject user using a rotating platform. Depth camera usage is primarily suitable for controllable environments and can also be applied to special environments with depth cameras integrated into computing devices (e.g., LIDAR-equipped on newer iPhones).

Next, the user head analysis unit (230) according to the first embodiment of the present invention will be described.

The user head analysis unit (230) detects a key point, such as the position and angle of the user's head, at least one of body parts like eyes, nose, mouth, ears, forehead, and hairline from the 2D head data obtained by capturing the user's head image, and maps them to the initially created user-customized 3D head data from the user head generation unit to analyze the image.

This is sequentially carried out through the 2D head image capturing step (231*a*), key point detection step (232), 3D head data mapping step (233), hair loss area determination step (234), and hair density information determination step (235).

The 2D head image capturing step (231*a*) serves to capture a 2D head image in which the user's hairline, for example, the forehead hairline, is visually observable within the face recognition area of the hair self-diagnosis application. In cases where the user's hairline is visually observable, no additional measures may be required; however, for a user whose hairline is not visually observable, at least a part of the user's hair, e.g., the forehead hair (the bangs), may be flipped to the rear relative to the front of the user's head, in the suspected hair loss area, e.g., in a direction opposite to the area where the forehead hairline is located so that the hairline is visually observable. Alternatively, various measures can be taken by those skilled in the art to make the hairline more visually observable, such as shaving the hair.

In the 2D head image capturing step (231*a*), not only one but multiple images can be captured, which can complement each other. For example, in the 2D head image capturing step (231*a*), not only a 2D head image in which at least a part of the user's hair is flipped in the opposite direction of the hair loss suspected area, but also a 2D head image in which at least a part of the hair is not flipped in the opposite direction of the hair loss suspected area can be captured.

The key point detection step (232) serves to detect at least one key point information from the overall facial outline and angle, and the user's body parts such as eyes, nose, mouth, ears, forehead, and hairline in the head image captured in the 2D head image capturing step.

The 3D head data mapping step (233) serves to map the 2D head image with detected key point information to the user-customized 3D head data generated in the user head generation unit. In the 3D head data mapping step (233), the user's head key points can be used to calibrate 3D data of the user's head part captured at different angles as if they were captured at the same angle.

The hair loss area determination step (234) serves to extract hairline contour information from the user image mapped in the 3D head data mapping step, compare the user hairline contour information and the recommended hairline contour information, and identify a hair loss boundary area delineated by at least one hairline. For example, the hair loss boundary area can be delineated by one hairline, but it can also be delineated by two or more hairlines, such as a first hairline and a second hairline.

The hair density information determination step (235) serves to enlarge automatically the hairline contour part of the hair, face, and skin tissue in the mapped user image, detect the endpoints of the hair emerging from the scalp, and measure the hair density by grasping the average number of hairs distributed per scalp area.

Alternatively, a user head analysis unit (230) according to a second embodiment of the present invention is described.

The user head analysis unit (230) according to the second embodiment captures and stores 3D head information of each identification ID from the identification ID input unit and detects at least one key point information of user's body parts such as eyes, nose, mouth, ears, forehead, and hairline to analyze user-customized 3D head data, by which sequentially carried out are a 3D head image capturing step (231*b*), hair loss area determination step (234), and hair density information determination step (235).

Here, the 3D head image capturing step (231*b*) serves to capture a 3D head image with the bangs flipped backward so that the user's front hairline is visually observable within the facial recognition area of the hair self-diagnosis application. In addition, in the 3D head image capturing step (231*b*), a 3D head image in which the hair is not flipped backward can also be captured.

As previously explained in the first embodiment, this is done through the initial head image capturing mode and the initial image interpolation capturing mode of the hair self-diagnosis application.

In cases where unclear 3D depth information is captured in the 3D head image capturing step (231*b*), the race-specific standard head information most similar to the 3D head image capturing information can be detected based on the unclear 3D head image, and the user's head part that has not been captured can be interpolated by matching the 3D head direction capture information with the detected head information. The race-specific standard head information most similar to the 3D head image capturing information can be detected, for example, based on big data stored in a hair self-diagnosis application server or web server.

This allows for the detection of head information of the form closest to the user, and thus, the acquisition of a 3D virtual head image of the user's head shape with minimized error range, even with unclear 3D head image capturing information.

As such, the 3D user head information obtained by each individual through the hair self-diagnosis service device (1) can be additionally stored in the hair self-diagnosis application server or web server, and can be used as big data information for user head information captured later.

Subsequently, the user head analysis unit (230) according to the second embodiment performs the hair loss area determination step (234) and the hair density information determination step (235) as described earlier for the first embodiment.

In this way, the user head analysis unit (230) according to the first and second embodiments of the present invention can map the user's head and hairline images captured in 2D form to 3D head data, or capture head depth information, forehead hairline information, and hair density information using a depth camera, minimizing the number of hairs needed for the hair transplant required area, and can propose a forehead hairline that fits harmoniously with the user's overall head shape and the position and proportion of the eyes, nose, and mouth.

Next, the hairline recommendation unit (240) according to the present invention is described.

The hairline recommendation unit (240) can be configured based on big data stored in a hair self-diagnosis application server or web server, for example, but not limited to, reflecting at least one of the user's current hair position, race, gender, age, and captured user head image to detect a virtual facial shape similar to the user, automatically matching multiple images of forehead hairlines suitable for the virtual facial shape and recommending them in ranked order, and allowing the user to select either one of the recommended ranked images of the forehead hairline or another image of the forehead hairline.

Hairline recommendations can be based on big data analysis, machine learning, or rule-based algorithms, and are not limited to the methods mentioned in this specification.

Also, the hairline recommendation unit (240) does not necessarily require a separate application server or web server, as an alternative, the hairline recommendation unit (240) can be independently installed on the hair self-diagnosis service device (1) or the hair self-diagnosis application (200).

Alternatively, the hairline recommendation unit (240) can provide a predefined user interface to allow the user to set the hairline directly.

This involves performing a virtual face detection step (241), hairline automatic setting step (242), hairline selection step (243), hair transplant area determination step (244), and required hair count prediction step (245) sequentially.

Firstly, the virtual face detection step (241) can serve to detect the virtual face shape that is most similar based on at least one shape image of the user's facial contour line, body parts such as eyes, nose, mouth, ears, forehead, and hairline, detected from the hair density automatic analysis unit. For example, the most similar virtual face shape can be detected from the big data stored in the hair self-diagnosis application server or web server.

Alternatively, the virtual face detection step (241) can perform the role of detecting the most similar virtual face shape to the preset virtual face shape, based on at least one image of the user's facial outline shape and body parts, such as eyes, nose, mouth, ears, forehead, and hairline, detected by the user's head analysis unit.

The detection of virtual faces can be based on big data analysis, machine learning, or rule-based algorithms, and is not limited to the methods mentioned in this disclosure.

Secondly, the hairline automatic setting step (242) serves to sequentially compare the ranks of virtual forehead hairline suitable for the virtual face detected in the virtual face detection step.

Thirdly, the hairline selection step (243) allows the user to directly select a forehead hairline among the virtual forehead hairlines that were sequentially compared in the hairline automatic setting step.

Fourthly, the hair transplant area determination step (244) applies the hairline selected in the hairline selection step to the user's head image, and measures the difference area between the user's hairline and the selected or set virtual hairline. For example, in the case of bangs, in the hair transplant area determination step (244), the bangs hairline may be applied to the user's face image to measure the difference area in the area of the forehead between the user's bangs hairline and the selected or set virtual bangs hairline.

Fifthly, the required hair count prediction step (245) predicts the required hair count by comparing the hair density information measured by the hair density automatic analysis unit with the area of the difference measured in the hair transplant area determination step, for instance, the area of the forehead.

According to the present invention, the hairline recommendation unit (240) detects the most similar virtual face shape to the user's head, sequentially compares suitable hairlines, allows the user to directly select or set the hairline, and determines the hair transplant required area by comparing the selected or set hairline to the user's forehead hairline; it can relatively accurately predict the required number of hairs tailored to the user based on 3D depth information, allowing users to self-diagnose hair loss without consulting a hair loss specialist, encourage the prevention of hair loss by periodically checking the progress of hair loss, and can heighten the need for hair transplantation as hair loss progresses.

Next, the required hair count prediction unit (250) according to the present invention will be described.

The required hair count prediction unit (250) measures the hair-required area compared to the user's hair density by contrasting the forehead hairline according to the hair density automatic analysis unit and hairline recommendation unit or the head analysis unit for the user with the set identification ID, and predicts and guides the required hair count.

Also, the hair self-diagnosis application (200) according to the present invention includes an event unit (260).

This includes a point accumulation unit (261) and a discount event unit (262).

The point accumulation unit (261) mentioned above allows users to be additionally granted a member-exclusive identification ID when a user receives a diagnosis and surgery at an affiliated hospital linked with the hair self-diagnosis application, and to accumulate points by logging in with the member-exclusive identification ID; this includes the attendance point accumulation unit (261*a*), advertisement playback point accumulation unit (261*b*), purchase point accumulation unit (261*c*), quiz point accumulation unit (261*d*), and referral code accumulation unit (261*e*).

The attendance point accumulation unit (261*a*) accumulates attendance points by logging in with the identification ID in which the user's data is stored and attending each day.

The advertisement playback point accumulation unit (261*b*) accumulates points at the end of advertisement playback provided by the affiliated hospitals.

The purchase point accumulation unit (261*c*) displays a list of hair loss prevention supplies from affiliated hospitals to form user-recommended product advertisements, and accumulates points upon purchasing products on the list during point accumulation events.

The quiz point accumulation unit (261*d*) displays various information related to hair loss prevention and accumulates points when users correctly answer hair loss prevention-related quizzes.

The referral code accumulation unit (261*e*) accumulates points in each of the member-exclusive IDs for both the user and the third party who received a member-exclusive ID by referral or introduction when the third party inputs the user's referral code.

The discount event unit (262) forms advertisements by displaying a list of affiliated hospitals and creates discount events by deducting accumulated points from the point accumulation unit upon visiting the affiliated hospitals.

The event unit (260) according to the present invention allows users to self-diagnose hair loss by evaluating their hairline status at regular intervals, encourages the use of the hair self-diagnosis application through various events, prevents further hair loss progression by providing hair care solutions through quizzes, and provides advertising marketing effects and patient recruitment effects for the linked hospitals and hair loss product sellers of the hair self-diagnosis application.

Hereinafter, a method for executing an application that improves the accuracy of hair self-diagnosis according to the present invention and the specific operation process of the hair self-diagnosis service device (1) are described.

First, secure the smart device to the smart device support holder of the hair self-diagnosis body, and connect the depth camera, smart device, and capturing switch through the camera receiving device wirelessly or wired.

Next, the user grips the handles located on the left and right sides of the hair self-diagnosis body, positions the depth camera so that the overall face and frontal hairline are visually observable, and pushes the capturing switch to capture a 3D image of the user's head, which is then saved on the smart device.

Next, the user is assigned individual identification ID information through the identification ID input unit of the hair self-diagnosis application, and enters user information into the assigned identification ID. The captured 3D image data can also be stored on a web server.

Next, a 2D image of the user's head, i.e., at least one or an arbitrary direction image of the user's head is captured within the facial recognition area of the hair self-diagnosis application, such as a left image, left-front image, front image, right-front image, right image, frontal upper image, and top image.

At this time, if at least one of the user's body parts, such as eyes, nose, mouth, ears, forehead, and hairline, is identified within the facial recognition area and the angle of each part of the head image deviates, or if out of focus or image shaking is detected in each part's image of the head automatically scanned and captured during the directional head image capturing step, the user is guided to recapture the head images to be required to be recaptured.

Next, the user's directional head part images, captured in 2D, are transformed and integrated into one coordinate system based on x, y, and z-axis positional coordinates, initially creating the user-customized 3D head data.

Next, a 2D head image is captured in the state of brushing the forehead hair backwards, making the user's forehead hairline visually observable within the facial recognition area of the hair self-diagnosis application. Alternatively, both a 2D head image with the forehead hair moved backward and a 2D head image with the forehead hair not moved backward can be captured.

At this point, the captured 2D head data is mapped to user-customized 3D head data, the user's hairline contour information is compared with the recommended hairline contour information, a hair loss boundary area delineated by at least one hairline is specified, and the hair density is measured by recognizing the average number of hairs distributed per scalp area.

As an alternative to the first embodiment using 2D images, the second embodiment detects at least one image of the user's facial shape, body parts, such as eyes, nose, mouth, ears, forehead, and hairline, from the 3D user head image data, and automatically enlarges the hairline boundary line between the hair, face, and skin tissues in the user's head image area to detect the endpoint of hair emerging from within the scalp; the hair density is then measured by determining the average number of hairs distributed per scalp area.

Next, for example, set based on the big data stored on a web server but not limited to this, the current position of the user's hair, ethnicity, gender, age, and head image of the user, e.g., body parts of the user, including at least one of the user's eyes, nose, mouth, ears, forehead, and hairline, are reflected to detect a virtual facial shape similar to the user; the system automatically matches multiple forehead hairline images suitable for the virtual facial shape and recommends them in rank order, and the user chooses from the recommended ranked forehead hairline images.

Lastly, the forehead hairline image selected by the user and the actual forehead hairline are compared to measure the hair-required area relative to hair density, and the required number of hairs is predicted and informed.

At this point, the user receives a recommendation for an affiliated hospital linked with the hair self-diagnosis application and earns points through various events to receive discounts.

LIST OF REFERENCE NUMERALS

100: Hair self-diagnosis body
110: Depth camera fixing frame
120: Smart device support holder
130: Camera receiver
140: Handle 150: Capturing switch
200: Hair self-diagnosis application
210: Identification ID input unit
220: User head generation unit
221: Directional head image capturing step
222: Re-capturing guidance step
223: 3D data generation step
224: Coordinate transformation step
225: User head stereoscopic information generation step
226: Forehead hairline fine-tuning step
230: User head analysis unit
231*a*, 231*b*: 2D head image capturing step
232: Key point detection step
233: 3D head data mapping step
234: Hair loss area determination step
235: Hair density information determination step
240: Hairline recommendation unit
241: Virtual face detection step
242: Hairline automatic setting step
243: Hairline selection step
244: Hair transplant area determination step
245: Required hair count prediction step
250: Required hair count prediction unit
260: Event unit
261: Point accumulation unit
262: Discount event unit

What is claimed is:

1. A method for executing, by one or more processors of a smart device, a hair self-diagnosis application to enhance hair self-diagnosis accuracy, the method comprising:

(a) capturing, within a facial recognition area of the hair self-diagnosis application, at least one user head image to obtain user head image information including measured depth information and captured hairline information of a user;

(b) evaluating the at least one user head image to detect at least one of an angle deviation and an image quality issue in the at least one user head image;

(c) automatically determining hair density on a user's head part based on the user head image information;

(d) performing at least one of: (1) recommending, for user selection, one or more hairlines suitable for the user's facial shape, or (2) receiving, from the user, input that directly sets a hairline;

(e) providing, on a display of the smart device, an image of: (1) a selected hairline that is selected by the user from the one or more recommended hairlines, or (2) the set hairline;

(f) determining a hair-required area based on a comparison between a user hairline corresponding to the user head image information and the selected hairline or the set hairline;

(g) computing and providing a required number of hairs according to the hair-required area and the determined hair density;

(h) detecting key point information from at least one body part constituting the user's head part to analyze user-customized 3D head data; and (i) identifying a virtual facial shape similar to the user by considering at least one of the user's current hair position, race, gender, age, and the at least one user head image, and automatically matching multiple hairline images suitable for the virtual facial shape and recommending the multiple hairline images in an order of ranking to enable the user to select one hairline image from the recommended multiple hairline images.

2. The method of claim 1, wherein the obtaining of the user head image information comprises generating a 3D user head image by at least one of:

capturing panoramic or directional stepwise 2D multi-angle head data of the user's head from left to right or from front to top, identifying a stereoscopic shape of the user's head based on the captured 2D multi-angle head data to generate the 3D user head image, and detecting key point information from at least one body part constituting the user's head part to initially generate user-customized 3D head data; and capturing the 3D user head image by a depth camera to generate 3D head data;

wherein evaluating the at least one user head image includes:

providing recapture guidance when at least one of the angle deviation and the image quality issue is detected.

3. The method of claim 2, wherein the capturing of the 2D multi-angle head data comprises:

a directional head image capturing step that captures at least one image of the user's head viewed in at least one direction within a facial recognition area of the hair self-diagnosis application;

a 3D data generation step that detects x-axis, y-axis, and z-axis positional coordinates at each location in a reference coordinate system from the at least one captured image of the user's head and formulates the positional coordinates in a 3D data format;

a coordinate transformation step that transforms the positional coordinates of the at least one image into a single coordinate system;

a user head stereoscopic information generation step that generates 3D user head stereoscopic information based on the at least one image transformed into the single coordinate system; and a hairline fine-tuning step that performs fine-tuning of 3D information of the user's head part and a hairline area from the 3D user head stereoscopic information.

4. The method of claim 1, wherein the determining hair density comprises:

a 2-dimensional head image capturing step that captures at least one 2-dimensional head image wherein the user's hairline is visually observable within a facial recognition area of the hair self-diagnosis application;

a key point detection step that detects an overall facial outline and angle, and key point information of at least one body part constituting the user's head part from the at least one 2-dimensional head image captured in the 2-dimensional head image capturing step;

a 3D head data mapping step that maps the 2-dimensional head image with detected key point information onto the user-customized 3D head data to generate a mapped user image;

a hair loss area determination step that calculates user hairline contour information in the mapped user image, compares the user hairline contour information with contour information of a recommended hairline, and identifies a hair loss boundary area delineated by at least one hairline, and a hair density information determination step that automatically enlarges a hairline contour region including hair, face, and skin tissue in the mapped user image, detects endpoints of hairs emerging from the user's scalp, and measures hair density by determining an average number of hairs distributed per scalp area.

5. The method of claim 1, wherein the obtaining of the user head image information comprises capturing at least one 3D head image where the user's hairline is visually observable within a facial recognition area of the hair self-diagnosis application and generating a mapped user image from the at least one 3D head image, and wherein the determining hair density comprises:

a hair loss area determination step that calculates user hairline contour information from the mapped user image, compares the user hairline contour information with contour information of a recommended hairline, and identifies a hair loss boundary area delineated by at least one hairline, and a hair density information determination step that automatically enlarges a hairline contour region including hair, face, and skin tissue in the mapped user image, detects endpoints of hairs emerging from the user's scalp, and measures hair density by determining an average number of hairs distributed per scalp area.

6. The method of claim 4, wherein the recommending comprises:

a virtual facial shape detection step that identifies and retrieves a virtual facial shape most similar to the user's facial shape by performing a comparative analysis between key points extracted from the at least one user head image and a plurality of pre-stored facial shapes, wherein the pre-stored facial shapes are set based on an image of at least one body part constituting the user's head part and the user's facial outline shape;

a hairline automatic setting step that ranks and displays a plurality of recommended virtual hairlines suitable for the identified virtual facial shape;

a hairline selection step that processes a user input signal selecting a specific hairline from the displayed recommended virtual hairlines to be applied to the at least one user head image;

a hair transplant area determination step that applies the selected hairline to the at least one user head image and measures a difference area between the user hairline and the selected virtual hairline; and a required hair count prediction step that calculates the required number of hairs for transplantation by executing an operation that applies the measured hair density, derived from the user head image information, to the measured difference area.

7. A hair self-diagnosis service device, comprising:

a smart device including one or more processors, a memory storing instructions, a display, and an input interface; and a hair self-diagnosis application stored in the memory and executed by the one or more processors to:

(i) capture, within a facial recognition area of the hair self-diagnosis application, at least one user head image to obtain user head image information including measured depth information and captured hairline information of a user;

(ii) evaluate the at least one user head image to detect at least one of an angle deviation and an image quality issue in the at least one user head image;

(iii) automatically determine hair density on a user's head part based on the user head image information;

(iv) perform at least one of: (a) recommending, for user selection, one or more hairlines suitable for the user's facial shape, or (b) receiving, from the user, input that directly sets a hairline;

(v) provide, on the display, an image of: (a) a selected hairline that is selected by the user from the one or more recommended hairlines, or (b) the set hairline;

(vi) determine a hair-required area based on a difference area between a user hairline and the selected hairline or the set hairline; and (vii) calculate and provide a required number of hairs according to the hair-required area and the determined hair density;

wherein the application is further executed to:

(viii) detect key point information from at least one body part constituting the user's head part to analyze user-customized 3D head data, and (ix) identify a virtual facial shape similar to the user by considering at least one of the user's current hair position, race, gender, age, and the at least one user head image, and automatically matching multiple hairline images suitable for the virtual facial shape and recommending the multiple hairline images in an order of ranking to enable the user to select one hairline image from the recommended multiple hairline images.

8. The device of claim 7, wherein the application is further executed to generate a 3D user head image by at least one of:

capturing panoramic-shaped or directionally-stepwise 2D multi-angle head data by photographing the user's head from left to right or from front to top, identifying a stereoscopic shape of the user's head based on the captured 2D multi-angle head data, generating the 3D user head image, detecting key point information from at least one body part constituting the user's head part, and initially generating user-customized 3D head data; and capturing the 3D user head image by a depth camera to generate 3D head data;

wherein evaluating the at least one user head image includes:

providing recapture guidance when at least one of the angle deviation and the image quality issue is detected.

9. The device of claim 7, wherein the application is further executed to:

capture at least one 2D head image in which the user's hairline is visually observable within a facial recognition area;

detect an overall facial outline and angle and key point information from at least one body part constituting the user's head part;

map the 2D head image having detected key point information onto the user-customized 3D head data to generate a mapped user image;

identify a hair loss boundary area delineated by at least one hairline by comparing user hairline contour information with contour information of a recommended hairline; and measure hair density by detecting endpoints of hairs emerging from the user's scalp by enlarging a hairline contour region including hair, face, and skin tissue in the mapped user image, and by determining an average number of hairs distributed per scalp area.

10. The device of claim 7, wherein the application is further executed to:

capture at least one 3D head image in which the user's hairline is visually observable within a facial recognition area:

identify a hair loss boundary area delineated by at least one hairline by calculating user hairline contour information in a user image and comparing the user hairline contour information with contour information of a recommended hairline; and measure hair density by enlarging a hairline contour region including hair, face, and skin tissue in the user image, detecting endpoints of hairs emerging from the user's scalp, and determining an average number of hairs distributed per scalp area.

11. The device of claim 7, wherein the application is further executed to:

identify and retrieve a virtual facial shape most similar to the user's facial shape by performing a comparative analysis between key points extracted from the at least one user head image and a plurality of pre-stored facial shapes, wherein the pre-stored facial shapes are set based on an image of at least one body part constituting the user's head part and the user's facial outline shape;

rank and display a plurality of recommended virtual hairlines suitable for the identified virtual facial shape;

process a user input signal selecting a specific hairline from the displayed recommended virtual hairlines to be applied to the at least one user head image;

apply the selected hairline to the at least one user head image and measure a difference area between the user hairline and the selected virtual hairline; and calculate the required number of hairs for transplantation by executing an operation that applies the measured hair density, derived from the user head image information, to the measured difference area.

12. The method of claim 5, wherein the recommending comprises:

a virtual facial shape detection step that identifies and retrieves a virtual facial shape most similar to the user's facial shape by performing a comparative analysis between key points extracted from the at least one user head image and a plurality of pre-stored facial shapes, wherein the pre-stored facial shapes are set based on an image of at least one body part constituting the user's head part and the user's facial outline shape;

a hairline automatic setting step that ranks and displays a plurality of recommended virtual hairlines suitable for the identified virtual facial shape;

a hairline selection step that processes a user input signal selecting a specific hairline from the displayed recommended virtual hairlines to be applied to the at least one user head image;

a hair transplant area determination step that applies the selected hairline to the at least one user head image and measures a difference area between the user hairline and the selected virtual hairline; and a required hair count prediction step that calculates the required number of hairs for transplantation by executing an operation that applies the measured hair density, derived from the user head image information, to the measured difference area.

* * * * *